United States Patent [19]

Ward, Jr.

[11] Patent Number: 4,920,063

[45] Date of Patent: * Apr. 24, 1990

[54] PROCESS FOR DETECTION OF SELECTED MOTILE ORGANISMS

[75] Inventor: N. Robert Ward, Jr., Seattle, Wash.

[73] Assignee: BioControl Systems, Inc., Bothell, Wash.

[*] Notice: The portion of the term of this patent subsequent to Jan. 7, 2003 has been disclaimed.

[21] Appl. No.: 773,201

[22] Filed: Sep. 9, 1985

Related U.S. Application Data

[63] Continuation-in-part of Ser. No. 621,182, Jun. 15, 1985, Pat. No. 4,563,418, which is a continuation of Ser. No. 366,978, Apr. 9, 1982, abandoned.

[51] Int. Cl.$^5$ .................. G01N 33/00; C12Q 1/20
[52] U.S. Cl. ................................ 435/7; 435/29; 435/33; 435/34; 435/879; 436/519; 436/20
[58] Field of Search .............. 435/7, 29, 33, 34, 879; 436/20, 519

[56] References Cited

U.S. PATENT DOCUMENTS 4,053,362 10/1977 Sforza .

FOREIGN PATENT DOCUMENTS 739102 6/1980 U.S.S.R. .

OTHER PUBLICATIONS

Dahlquist et al., "Studies of Bacterial Chemotaxis in Defined Concentration Gradients. A Model for Chemotaxis Toward L-Serine", *J. Supremol. Strut.*, 4:329-42 (1976) (Abst. only).
Harvey et al., "A Method of Secondary Enrichment for Salmonellas Independent of Selective Toxic Chemicals", J. Hyg. Camb. 64:361-366, 1966.
Lennette et al., "Manual of Clinical Microbiology", 2nd edition, American Society for Microbiology, 1974, p. 194.
Davis et al., "Microbiology", 2nd edition, 1973, pp. 386-387.
Abrahamsson et al., "Detection of Salmonella by Single-Culture Technique", Appl. Microbiol., vol. 16, pp. 1695-1698 (1968).
J. Adler, "Effect of Amino Acids and Oxygen of Chemotaxis in Escherichia Coli", Journal of Bacteriology 92:121-129 (1966).
J. Adler, "Chemotaxis in Bacteria", Science 153:708-716 (1966).
Banwart, "Rapid Detection of Salmonella in Turkey Rolls and on Fresh Chicken Parts", Poultry Science 48:1528-1532 (1969).
Banwart, G. J., "Glassware Apparatus for Determining Motile Bacteria", Poultry Science, pp. 1209-1212, 1967.
Banwart et al., "Rapid Determination of Salmonella in Samples of Egg Noodles, Cake Mixes and Candies", Applied Microb 18:83-842, 1969.
J. A. Barkate, "Screening of Feed Components for Salmonella with Polyvalent H Agglutination", Appl. Microb. 16:1872-1874 (1968).

(List continued on next page.)

Primary Examiner—Robert J. Warden
Assistant Examiner—Richard Wagner
Attorney, Agent, or Firm—Seed and Berry

[57] ABSTRACT

Methods and associated devices for detecting the presence of a particular motile organism within a sample are disclosed. The sample may be derived from dry milk, raw meat, poultry or a clinical specimen. A preferred method includes inoculating a selective enrichment medium containing a chemotactic attractant with the sample and contacting the selective enrichment medium with a nonselective motility medium containing a chemotatic attractant in a concentration less than the attractant concentration in the selective enrichment medium. Upon incubation, the motile organism metabolizes the chemotactic attractant, allowing the organism to move into the motility medium where it interacts with antibodies specific for the organism, thereby causing the formation of a persistent immobilization band. The methods are particularly useful in detecting Salmonella.

21 Claims, 1 Drawing Sheet

OTHER PUBLICATIONS

Chau, P. Y. et al., "A Simple Procedure for Screening of Salmon Ellae Using a Semi-Solid Enrichment and a Semi-Solid Indicator Medium", Journal of Applied Bacteriology 41:283-294 (1976).

Fung et al., "A Rapid and Simple Method for the Detection and Isolation of Salmonella from Mixed Cultures and Poultry Products", Poultry Sci. 49:46-54 (1970).

Harper et al., "A Selective Motility Medium for Routine Isolation of Salmonella", J. Hyg. Cambridge 67:181-186 (1969).

Harvey et al., "The Isolation of Salmonellas from Animal Feedingstuffs", J. Hyg. Calmb. 65:237-244 (1967).

Mohit, B., "Disc Immuno-Immobilization Method for Simultaneous Typing and Isolation of Salmonella Flagellar Phases", J. of Bact. 96:106-164 (1968).

Mohit et al., "A Simple Single-Step Immunoimmobilization Method for the Detection of Salmonella in the Presence of Large Numbers of Other Bacteria", J. Med. Microbiol. 98:173-176 (1975).

Silliker et al., "Polyvalent H Agglutination as a Rapid Means of Screening Non-Lactose-Fermenting Colonies for Salmonella Organisms", The Ame. Journal of Clinical Pathology 43:548-554 (1965).

Stuart et al., "Isolation of Salmonellae by Selective Motility Systems", Appl. Microbiol. 13:365-372 (1968).

Swaminathan et al., "Rapid Detection of Salmonellae in Foods by Membrane Filter-Disc Immunoimmobilization Technique", J. of Food Science 43:1444-1447 (1978).

PROCESS FOR DETECTION OF SELECTED MOTILE ORGANISMS

CROSS-REFERENCE TO RELATED APPLICATION

This application is a continuation-in-part of applicant's copending application Ser. No. 621,182, filed June 15, 1985, now U.S. Pat. No. 4,563,418, which application is a continuation of Ser. No. 366,978, filed Apr. 9, 1982, now abandoned.

TECHNICAL FIELD

The present invention relates to the detection of organisms within samples in general, and more specifically, to a method for the detection of a particular motile organism in a sample, for example, flagellate bacteria such as Salmonella.

BACKGROUND ART

Salmonella is a genus of a facultative aerobic gram-negative flagellate bacteria which may be found in a variety of foodstuffs, dairy products, feed, water and wastewater, and which are a cause of various pathological conditions in man. Salmonellosis, a food-associated disease, is a major problem in the United States because of its incidence, economic significance, and hazardous nature. Salmonellosis is usually not a fatal disease, although some fatalities have been reported in infants and the aged.

Food, dairy and feed industries intensively scrutinize their products for Salmonella contamination because of the economic impact of recalling and destroying contaminated products and the potential loss of confidence by consumers concerning product safety.

Testing of products for Salmonella contamination is complicated due to the fact that the organism is commonly present in very low levels. Further complicating the task of detection of the Salmonella is the presence of numerous other microorganisms, including competitive flagellate species, typically present in foodstuffs and animal feeds, that can interfere with the cultural detection of the microorganism.

There are a number of disadvantages associated with the conventional detection procedures for Salmonella. The cultural procedures are cumbersome and labor-intensive to perform, require expensive laboratory materials, are lengthy (requiring up to four days to complete), and may yield false negative results. The fluorescent antibody technique requires highly trained personnel, expensive fluorescent microscopic systems, and costly fluorescein-labeled antisera, which at times lack specificity.

Several attempts have been made to devise other rapid and simple methods for the detection of Salmonella. Some of these methods involve preferential migration of Salmonella through a selective semi-solid motility medium. Mohit et al., in "A Simple Single-Step Immunoimmobilization Method for the Detection of Salmonella in the Presence of Large Numbers of Other Bacteria," *J. Med. Microbiol.*, Vol. 8, page 173 (1975), and Swaminathan et al., in "Rapid Detection of Salmonella in Foods by Membrane Filter-Disc Immobilization Technique," *J. Food Science,* Vol. 43, No. 5, p. 144 (1978), describe selective semisolid media which promote the migration of Salmonella in a petri dish followed by immobilization using polyvalent H antisera. Swaminathan et al. used a membrane filter to concentrate Salmonella from the primary selective enrichment before selective migration in order to increase recovery.

Although these motility techniques showed promise, operational difficulties compromised their effectiveness. In particular, problems included:

(1) the lack of definite and easily interpretable reactions to indicate the presence of Salmonella;

(2) the use of chemical agents in the motility medium to promote the selective migration of Salmonella which greatly reduced or completely inhibited motility of certain Salmonella strains; and (3) the use of intricate glassware arrangements which made setup and inoculation difficult and expensive.

Consequently, there is a need in the art for an improved method for detecting Salmonella or other particular motile organisms in a sample, which method (a) is sensitive and specific; (b) is rapid, microbiologically safe, relatively uncomplicated, and inexpensive; and (c) provides a definite and easily intepretable indication of the presence of Salmonella or the other particular motile organism to be detected. The present invention fulfills this need and further provides other related advantages.

DISCLOSURE OF INVENTION

Briefly stated, the present invention discloses methods and associated devices for detecting the presence of a particular motile organism within a sample, such as a sample derived from dry milk, raw meat, poultry, or a clinical specimen. In one aspect of the present invention, the method comprises inoculating a selective enrichment medium containing at least one chemotactic attractant with a sample containing the motile organism to be detected and one or more motile competitors. The chemotactic attractant causes motility inhibition of the motile organism to be detected and the motile competitors, while the enrichment medium is selective for the growth of the motile organism to be detected relative to the growth of the motile competitors. The selective medium containing the motile organism is contacted with a nonselective motility medium, the motility medium containing a chemotactic attractant in a concentration which is less than the attractant concentration in the selective enrichment medium. The sample/selective enrichment medium is then incubated under conditions which permit the motile organism to metabolize the chemotactic attractant to a level which is less than the attractant concentration in the motility medium, thereby relieving the motile organism from its motility inhibition, and allowing the motile organism to move into the motility medium. The motility medium further contains antibodies specific for the motile organism, the antibodies being restricted to essentially unidirectional movement within the motility medium from a position distal to the position of the motile organism. The antibodies are present in sufficient quantity to produce a persistent immobilization band upon interaction of the motile organism with the antibodies. Upon this interaction, one may observe the formation of the immobilization band, thereby signifying the presence of the particular motile organism. Depending upon the characteristics of the particular organism to be detected and the condition of the sample, it may be useful to enrich the sample in an enrichment medium, either nonselective or selective, prior to the inoculation step.

A related aspect of the present invention discloses a method substantially the same as that noted above, with the exception that the antibodies within the motility medium which are specific for the motile organism substantially surround the motile organism and are present in sufficient quantity to produce a persistent immobilization ring upon the interaction of the motile organism with the antibodies.

An additional aspect of the present invention discloses a motility vessel for use within a motility-immunoimmobilization assay, comprising a housing having two spaced end openings, each f the end openings having a removable cap thereon, the housing further defining a motility chamber and an enrichment chamber communicating with one another through a conduit. The enrichment chamber contains a selective enrichment medium and at least one chemotactic attractant. The motility chamber contains a nonselective motility medium and a chemotactic attractant in a concentration less than the attractant concentration in the enrichment chamber, the motility chamber further containing a quantity of antibodies positioned distal from the conduit.

Other aspects of the invention will become evident upon reference to the following detailed description and drawings.

BEST MODE FOR CARRYING OUT THE INVENTION

Figure 1:
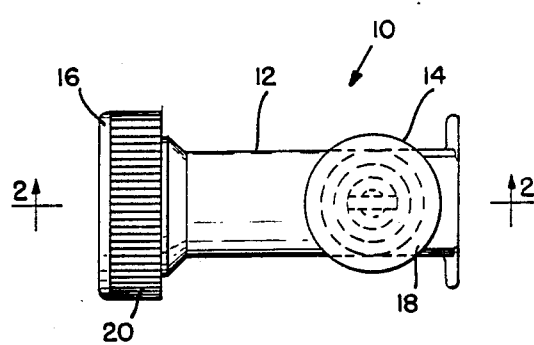
FIG. 1 is a top view of a motility vessel of the present invention.

Within the present invention, a particular organism present in a sample can be detected by a "motility-immunoimmobilization assay." Depending upon the number and physiological condition of the particular motile organisms and the number of the competitor microorganisms in the sample, different approaches may be taken. For example:

(i) If the sample contains few of the particular motile organisms and/or the sample has undergone processing, such as heat treatment, change in acidity or alkalinity, drying, etc., which usually results in the physiological injury of the bacteria present in the sample, the sample should be enriched in a nonselective enrichment medium. This medium generally contains only nutrients and vitamins, in order to promote the repair of injured bacteria and the subsequent growth of these organisms. An example of a nonselective enrichment broth commonly used is lactose broth. An example of such a sample is dry milk.

(ii) If the sample contains few of the particular motile organisms and greater numbers of competitor bacteria and the sample has not undergone any processing steps or experienced conditions detrimental to the survival of the microorganisms, then the sample should be selectively enriched in favor of the motile organism relative to the competitor bacteria. This selective enrichment medium is generally comprised of a mixture of nutrients, vitamins and chemical agents. These chemical agents (hereinafter "selective agents") either decrease the rate of growth of the competitor bacteria or kill the competitor bacteria, but concurrently allow the growth of the particular motile bacteria at a rate greater than the competitor bacteria. Examples of conventional selective enrichment media for Salmonella are tetrathionate broth, tetrathionate broth with 0.001% brilliant green, selenite-cystine, SBG-S, Rappaporte Vassiliadis broth, modified Rappaporte broth (RIO) (Vassiliadis et al., ZBL *Bakteriol. Mikroviol. Hyg. I ABT. Orig B* 173: 382–389, 1981), Lysine-Iron-Cysteine-Neutral Red Broth (LICNR), and modified LICNR broth (Hoben et al., *Applied Micro.* 25: 123–129, 1973). An example of such a sample is raw meat or poultry.

(iii) If the sample has a greater number of the particular motile organisms relative to the numbers of competitor organisms and the sample has not been exposed to conditions which would result in the physiological injury of the particular motile organism, the sample may be added to a selective enrichment broth to further increase the number of the particular motile organism relative to the competitor bacteria; or the sample may be added directly into a selective enrichment medium supplemented with a chemotactic agent, as more fully described below. The latter procedure would be particularly useful where the sample has been derived within a clinical setting from a patient, for example, who exhibits symptoms of an intestinal infection such as diarrhea. This procedure would be equally applicable in a veterinary setting.

Subsequent to the selective or nonselective enrichment of the sample, or in the absence of such a step as described above, the sample is added to a selective enrichment medium which contains a suitable chemotactic attractant. For the detection of Salmonella, the selective enrichment medium should comprise a conventional selective enrichment broth, such as tetrathionate broth, tetrathionate broth with 0.001% brilliant green, selenite-cystine broth or SBG-S broth. A preferred chemotactic attractant for Salmonella is L-serine. The concentration of L-serine in the selective enrichment medium should be greater than that which exists in the motility medium used in the motility vessel. This concentration is usually greater than 0.001 M, and preferably should be in the range of 0.001 M to 0.1 M.

Because of the presence of the chemotactic attractant in the selective enrichment medium and because of the greater concentration of the chemotactic attractant in the selective enrichment medium than in the motility medium, the particular motile organisms and their motile competitor bacteria present in the sample are substantially "paralyzed" for a period of time and are unable to undergo chemotactic-directed movement from the selective enrichment medium into the motility medium. The particular motile organisms and their competitors are unable to move from the selective enrichment medium into the nonselective enrichment medium until the concentration of the chemotactic attractant in the selective enrichment medium is reduced by metabolism by the particular motile bacteria and their competitors to a level such that a higher concentration of chemotactic attractant exists in the motility medium. At such a time, a temporal concentration gradient is established such that the particular motile organisms and motile competitor bacteria can recognize a higher concentration of the chemotactic attractant in the motility medium and these organisms can undergo chemotactic-directed movement.

The chemotactic attractant serves, then, to keep the motile organisms in the presence of the selective agents, where the particular motile organisms to be detected have a growth advantage for an appreciable period of time. The preferred concentration of the chemotactic attractant is one that is high enough to inhibit chemotactic-directed movement of motile organisms from the selective enrichment environment to the motility medium for approximately four hours.

When a sufficient amount of the chemotactic attractant has been metabolized, thereby relieving the motility inhibition, the motile organisms are free to move into the nonselective motility medium. In those samples in which the particular motile organisms are present, the particular motile organisms will generally grow at a higher rate than their competitor organisms in the selective enrichment medium and can rapidly metabolize the chemotactic attractant. In these cases, the motility inhibition is quickly relieved and the particular motile organism and its motile competitors can rapidly move into the nonselective motility medium. In those samples in which the particular motile organisms are not present, the competitor organisms grow at a rate which is substantially depressed in the presence of selective agents in the enrichment medium. This consequentially results in the inhibition of movement of the competitor motile bacteria into the nonselective motility medium during the period of time allotted for the test. This motility inhibition is particularly beneficial in those cases where the motile competitor bacteria may cross-react with the antisera to the particular bacteria and provide a false positive result.

The motility medium into which the motile organisms to be detected migrate is preferably nonselective. In other words, it contains no selective chemical agents to inhibit the growth of the competitive motile organisms relative to the growth of the particular motile organism to be detected. This is particularly important for Salmonella, as the use of a selective motility medium would greatly reduce or completely inhibit the motility of certain strains of Salmonella.

It is preferable that the motility medium contain a gelling agent, such as agarose. The gelling agent should be employed at a concentration which is low enough to allow rapid motility of the motile organisms, but high enough to form a gel. For example, a concentration in the range of 0.1–0.4 grams/100 mls is normally suitable.

The motility medium is also provided with a chemotactic agent or agents, to which the particular motile organisms to be detected and their competitors are attracted, along with nutrients such as amino acids and vitamins for the growth of the organisms. Where the motile organism to be detected is Salmonella, the attractant could be glucose, or if glucose is not present, could be serine. As noted above, L-serine has been identified as a chemotactic attractant of Salmonella and other motile nonsalmonellae competitors. When the motility-immunoimmobilization assay is performed in a completely enclosed vessel, the preferred motility medium should be free of nutrients, most notably carbohydrates, such as glucose. The presence of carbohydrates such as glucose cause the motile organisms to generate gas, which could result in disruption of the gel.

Also added to the motility medium are diffusible monoclonal or polyclonal antibodies specific to the flagella of the particular motile organisms to be detected. The antibodies should be added to the motility medium in a quantity which is sufficient to produce a permanent immobilization band upon interaction with the particular motile organisms. If the particular motile organism to be detected is Salmonella, there are a pool of commercially available antibodies specific to many different types of Salmonella flagella that can be used, such as polyvalent H antisera (Difco Laboratories, Detroit, Mich.; Lee Laboratories, Atlanta, Ga.). It will be evident to one skilled in the art that suitable monoclonal antibodies specific to the flagella of Salmonella may be substituted for polyclonal antibodies. For example, Salmonella may be immobilized by the MOPC 467 monoclonal antibody (Smith & Potter, *J. Immunol.* 144: 1847, 1975; Smith et al., *J. Immunol.* 123: 1715, 1979) or the 6H4 monoclonal antibody (Mattingly et al., *Food Technology* 39: 90–94, 1985).

It is important that the concentration of the chemotactic attractant in the motility medium be carefully controlled. When high levels of the attractant are employed, the rate of motility is slow because there is a significant amount of attractant to metabolize. However, the number of motile organisms responding to the chemotactic attractant is increased. Therefore, more of the particular motile organisms to be detected interact with the antibody, and the intensity of the band, as visually observed, is increased. In contrast, when very low levels of the chemotactic attractant are employed, the motility rate is very rapid, but the number of cells interacting with the antibody is proportionately decreased and the intensity of the band is diminished.

As the assay is completed in approximately 24 hours or less, it is usually completed before the motile competitors of the particular motile organisms, whose growth has been substantially inhibited by the selective agents in the selective enrichment medium, can move into the motility medium. This is advantageous because it reduces the potential for a false positive interpretation caused by certain motile competitors which may cross-react with the flagellar antibodies.

An adequate concentration of the chemotactic attractant in the motility media is therefore that concentration which results in both:

(1) a rate of motility in the motility medium which is rapid enough for the assay to be completed in a relatively short perod of time, for example, 24 hours or less; and (2) the formation of an intense, persistent and macroscopically discernible immobilization band following interaction of the particular motile organism with the diffused flagellar antibodies.

Preferred vessels for use in conjunction with the method described above, hereinafter referred to as "motility vessels," should have a transparent body, and may be, for example, in the form of a single-use, disposable unit made of transparent or optically clear plastic. Although it is preferable to use a plastic which is completely distortion-free (optically clear), use of a transparent plastic is more than adequate for purposes of the present invention. It is also preferable for that portion of the motility vessel into which the antibody is introduced to be designed such that the antibody will be substantially confined and the diffusion of the antibody into the motility medium is restricted and essentially unidirectional. By confining the antibody in this manner, an immobilization band, which forms by the interaction of the particular motile organisms to be detected and the antibodies, is substantially permanent rather than transient. As a safety consideration, it is preferable to completely seal the motility vessel after the addition of inoculum and antiserum.

Figure 2:
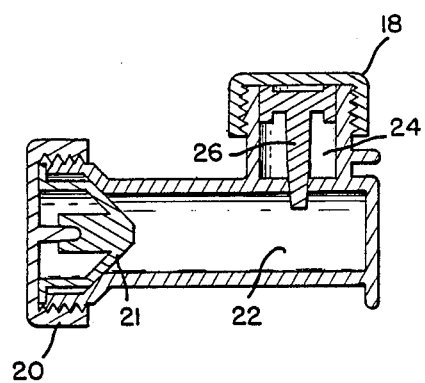
FIG. 2 is a vertical cross-sectional view taken substantially along the line 2—2 of FIG. 1.

Referring now to FIG. 1, a preferred form of a motility vessel of the present invention is shown. The motility vessel 10 comprises a housing 12 having a first end 14 and a second end 16, each of the ends being provided with end caps 18 and 20, respectively. Turning now to FIG. 2, the housing 12 defines a central motility chamber 22 and an enrichment chamber 24, connected by a conduit 26.

In order to utilize the motility vessel 10, motility medium is added to the motility chamber 22 upon removal of the end cap 20 from the end 16. The motility medium should be sterilized for use, preferably by heating at 121° C. for 15 minutes. The molten medium, cooled to 45° C., is then added to the motility vessel. In order to facilitate access into the motility chamber, it is preferable to provide the end 16 with a threaded collar 17, such that a mateable cap 20 may be screwed thereon. Enough medium should be added to substantially fill the central motility chamber. The cap 20 is then screwed onto the end 16. As shown in FIG. 2, it is preferable to provide the cap 20 with a gel displacer 21, in order to facilitate the expulsion of any gas bubbles from the motility chamber which might disrupt the gel. The gel displacer may be a part of or separate from the cap 20, and when designed in this manner, its use will result in the exclusion of gas bubbles as well as a small amount of motility medium from the chamber 22 upon securing the cap 20. The molten motility medium solidifies to a consistency which resembles a viscous fluid.

It is preferable, when inoculating the enrichment chamber 24 with the sample and selective enrichment medium containing the chemotactic attractant, to place the motility vessel in a horizontal position upon removal of the cap 18. Approximately 0.1 ml of the sample is generally added to the selective enrichment medium within the chamber 24, following which the cap 18 is replaced.

Subsequently, it is preferable to place the motility vessel in a substantially vertical position while the cap 20 is again removed. Antisera is then layered onto the exposed surface of the solidified motility medium within the chamber 22. An amount of antisera in the range of 20-100 microliters is preferable. The cap 20 is then replaced and the motility vessel incubated at a temperature between 32°-43° C., preferably 35°-37° C., while maintaining the vessel in a substantially vertical position.

The particular motile organisms to be detected, after metabolizing the chemotactic attractant added to the selective enrichment medium, move into the motility medium through the conduit 26 toward the end 16. The antisera which was added to the surface of the motility medium diffuses into the medium, where it immobilizes the motile organisms to be detected. This immobilization causes the formation of one or more sharp, dense, macroscopically visible bands approximately 1-2 mm below the edge of the end 16 where the antisera was added.

The following example is offered by way of illustration and not by way of limitation.

EXAMPLE

Tetrathionate broth with brilliant green was prepared according to the manufacturer's specifications. A 25 gram (g) sample of raw chicken liver was added to 225 ml of tetrathionate broth (Difco) with 0.001% brilliant green and the combination put into a blender and blended for 2 minutes. The blended sample/broth was then incubated at 35° C. for 24 hours (note: incubation may generally be carried out at 35°-43° C. for 8-48 hours).

A motility vessel as described above was sterilized, and the central motility chamber filled with sterile, molten, nonselective motility medium comprised of 1.5% (w/v) polypeptone (BBL, Cockeysville, MD) and 0.2-0.3% (w/v) agar. The medium was cooled to 45°-48° C. prior to filling the chamber. The motility medium within the chamber was then allowed to substantially solidify. (Note: the filled units may be stored up to 9 months before use if tightly capped to avoid dehydration.)

The motility vessel was then tipped approximately 90°, and the cap and gel displacer of the enrichment chamber removed. 0.9 ml of tetrathionate broth supplemented with 0.1 M L-serine was then added to the enrichment chamber. This enrichment medium was prepared according to the manufacturer's instructions. This medium contacts the nonselective motility medium within the motility chamber. Approximately 0.1 ml of selectively enriched sample was then inoculated into the serine-supplemented broth, and the cap replaced.

Upon returning the motility vessel to its upright position, the cap and gel displacer of the motility chamber were removed. Approximately 0.1 ml of 1:5 dilution of polyvalent H antibodies (Difco) was added to the surface of the exposed motility medium, and the cap replaced.

The motility vessel was then incubated for 8-24 hours and a thin opaque band(s) of cells approximately 1-22 mm below the motility medium surface which received the antibodies was observed.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for detecting the presence of a particular motile organism within a sample, comprising:
   inoculating a selective enrichment medium containing at least one chemotactic attractant with a sample containing the particular motile organism and one or more motile competitors, said chemotactic attractant causing motility cessation of the particular motile organism and the motile competitors within the selective enrichment medium, said enrichment medium being selective for the growth of the particular motile organism relative to the growth of the motile competitors;
   contacting the selective enrichment medium containing the motile organisms with a nonselective semisolid motility medium having a gel matrix, said semisolid motility medium containing said chemotactic attractant in a concentration which is less than said initial chemotactic attractant concentration in the selective enrichment medium, and wherein the gel matrix of the semisolid motility medium remains substantially intact;
   incubating the sample/selective enrichment medium under conditions which permit the motile organisms to metabolize said chemotactic attractant in said selective enrichment medium to a level which is less than said chemotactic attractant concentration in the semisolid motility medium, thereby allowing the motile organisms to move into the semisolid motility medium, said semisolid motility medium further containing antibodies specific for the particular motile organism, said antibodies being restricted to essentially unidirectional diffusion within the semisolid motility medium from a position distal to the position of the motile organisms and present in sufficient quantity to produce a persistent immobilization band upon interaction of the particular motile organism with the antibodies; and
observing the formation of the immobilization band.

2. The method of claim 1, including, prior to the inoculation step, enriching the sample in a pre-enrichment medium.

3. The method of claim 2 wherein said enrichment medium is a nonselective pre-enrichment medium.

4. The method of claim 2 wherein said pre-enrichment medium is selective for the growth of the particular motile organism to be detected relative to the motile competitors.

5. The method of claim 1 wherein the particular motile organism to be detected is Salmonella.

6. The method of claim 5 wherein said selective enrichment medium is selected from the group consisting of tetrathionate broth, tetrathionate broth with 0.001% brilliant green, selenite-cystine broth and SBG-S broth.

7. The method of claim 5 wherein said chemotactic attractant is L-serine.

8. The method of claim 7 wherein said chemotactic attractant is present in a concentration of between 0.001 M and 0.1 M.

9. The method of claim 2 wherein said sample is derived from the group consisting of dry milk, raw meat, poultry and clinical specimens.

10. The method of claim 1 wherein said sample is derived from a clinical specimen.

11. The method of claim 1 wherein said antibodies are selected from the group consisting of polyclonal and monoclonal antibodies.

12. The method of claim 11 wherein said polyclonal antibody is polyvalent H antisera.

13. The method of claim 1 wherein said semisolid motility medium contains a gelling agent.

14. The method of claim 13 wherein said gelling agent is agarose or agar.

15. The method of claim 1 wherein said semisolid motility medium is substantially free of nutrients which cause the motile organism or competitor organisms to produce gas.

16. A method for detecting the presence of a particular motile organism within a sample, comprising:
inoculating a selective enrichment medium containing at least one chemotactic attractant with a sample containing the particular motile organism and one or more motile competitors, said chemotactic attractant causing motility cessation of the particular motile organism and the motile competitors within the selective enrichment medium, said selective enrichment medium being selective for the growth of the particular motile organism relative to the growth of the motile competitors;
contacting the selective medium containing the motile organisms with a nonselective semisolid motility medium having a gel matrix, said semisolid motility medium containing said chemotactic attractant in a concentration which is less than said initial chemotactic attractant concentration in the selective enrichment medium, and wherein the gel matrix of the semisolid motility medium remains substantially intact;
incubating the sample/selective enrichment medium under conditions which permit the motile organisms to metabolize said chemotactic attractant in said selective enrichment medium to a level which is less than said chemotactic attractant concentration in the semisolid motility medium, thereby allowing the motile organisms to move into the semisolid motility medium, said semisolid motility medium further containing antibodies specific for the particular motile organism, said antibodies present in sufficient quantity to produce a persistent immobilization band upon interaction of the particular motile organism with the antibodies; and
observing the formation of the immobilization band.

17. The method of claim 16, wherein the semisolid motility medium contains a gelling agent.

18. The method of claim 17, wherein the gelling agent is agarose or agar.

19. A method for detecting the presence of a particular motile organism within a sample, comprising:
inoculating a selective enrichment medium with a sample putatively containing the particular motile organism and one or more motile competitors, said enrichment medium being selective for the growth of the particular motile organism relative to the growth of the motile competitors;
incubating the sample in selective enrichment medium at a permissive temperature to enhance the growth of the particular motile organism relative to the motile competitors;
inoculating a nonselective semisolid motility medium with the selective enrichment medium containing the motile organisms, said semisolid motility medium containing a chemotactic attractant;
incubating the inoculated semisolid motility medium under conditions which permit the motile organisms to metabolize the chemotactic attractant, thereby allowing the motile organisms to move through the semisolid motility medium, said semisolid motility medium further containing antibodies specific for the particular motile organism, said antibodies being restricted to essentially unidirectional diffusion within the semisolid motility medium from a position distal to the position of the inoculation of the motile organisms and present in sufficient quantity to produce a persistent immobilization band upon interaction of the particular motile organism with the antibodies; and
observing the formation of the immobilization band.

20. The method of claim 19 wherein the selective enrichment medium is selected from the group consisting of tetrathionate broth, tetrathionate broth with 0.001% brilliant green, selenite-cystine broth, and SBG-S broth.

21. The method of claim 19 wherein the particular motile organism is Salmonella.

* * * * *

UNITED STATES PATENT AND TRADEMARK OFFICE
CERTIFICATE OF CORRECTION

PATENT NO. : 4,920,063

DATED : April 24, 1990

INVENTOR(S) : N. Robert Ward, Jr.

It is certified that error appears in the above-identified patent and that said Letters Patent is hereby corrected as shown below:

Column 9:

In claim 3, line 1 should read "pre-enrichment" instead of enrichment, and line 3 should read "enrichment" instead of "pre-enrichment" to accurately reflect the amendment of September 6, 1989.

Signed and Sealed this

Thirteenth Day of April, 1993

Attest:

STEPHEN G. KUNIN

*Attesting Officer*   *Acting Commissioner of Patents and Trademarks*